(12) United States Patent
Shimizu et al.

(10) Patent No.: US 6,444,460 B1
(45) Date of Patent: Sep. 3, 2002

(54) MICROBIAL PRODUCTION OF ACTINOL

(75) Inventors: Sakayu Shimizu, Kyoto; Masaru Wada, Fukui-ken, both of (JP)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/375,129

(22) Filed: Aug. 16, 1999

(30) Foreign Application Priority Data

Aug. 19, 1998 (EP) .............................................. 98115564

(51) Int. Cl.⁷ .................................................. C12P 7/26
(52) U.S. Cl. ........................ 435/280; 435/148; 435/170
(58) Field of Search ................................. 435/280, 170, 435/148

(56) References Cited

U.S. PATENT DOCUMENTS 3,988,205 A   10/1976   Boguth et al.
5,385,833 A   1/1995    Bradshaw et al.

OTHER PUBLICATIONS

ATCC Catalogue of Bacteria, 1996, pp. 37 and 268.*
Goodfellow et al., "The Biology of the Actinomycetes", 1984, Academic Press, pp. 77–79.*
Kunio Nishii, et al., Microbial conversion of dihydrooxoisophorone (DOIP) to 4–hydroxy–2,2,6–trimethylcyclohexanone(4–HTMCH) by thermophilic bacteria,. J. of Biotech., vol. 9, pp. 117–128 (1989).
Takehisa Ohashi and Junzo Hasegawa, Practical Syntheses Using Biocatalysts., The Proceedings of the Symposium "Molecular Chirality 1996," Tokyo, Japan, pp. 47–50 (1996).

* cited by examiner

*Primary Examiner*—Irene Marx
(74) *Attorney, Agent, or Firm*—Bryan Cave LLP

(57) ABSTRACT

A process for making (4R, 6R)-4-hydroxy-2,2,6-trimethylcyclohexanone by contacting (6R)-2,2,6-trimethylcyclohexanedione with a microorganism which is selected from microorganisms of the genera Cellulomonas, Corynebacterium, Planococcus and Arthrobacter and which is capable of the selective asymmetric reduction of (6R)-2,2,6-trimethylcyclohexanedione to (4R, 6R)-4-hydroxy-2,2,6-trimethylcyclohexanone, and recovering the resulting (4R, 6R)-4-hydroxy-2,2,6-trimethylcyclohexanone from the reaction mixture. The selective asymmetric reduction can be effected in the presence of a co-factor, such as, nicotinamide adenine dinucleotide (NAD), nicotinamide adenine dinucleotide phosphate (NADP), or said co-factor with glucose and glucose dehydrogenase (GDH), and/or in the presence of a surfactant. The product is useful for the synthesis of carotenoids, such as, zeaxanthin.

2 Claims, 2 Drawing Sheets

MICROBIAL PRODUCTION OF ACTINOL

FIELD OF THE INVENTION

Figure 1:
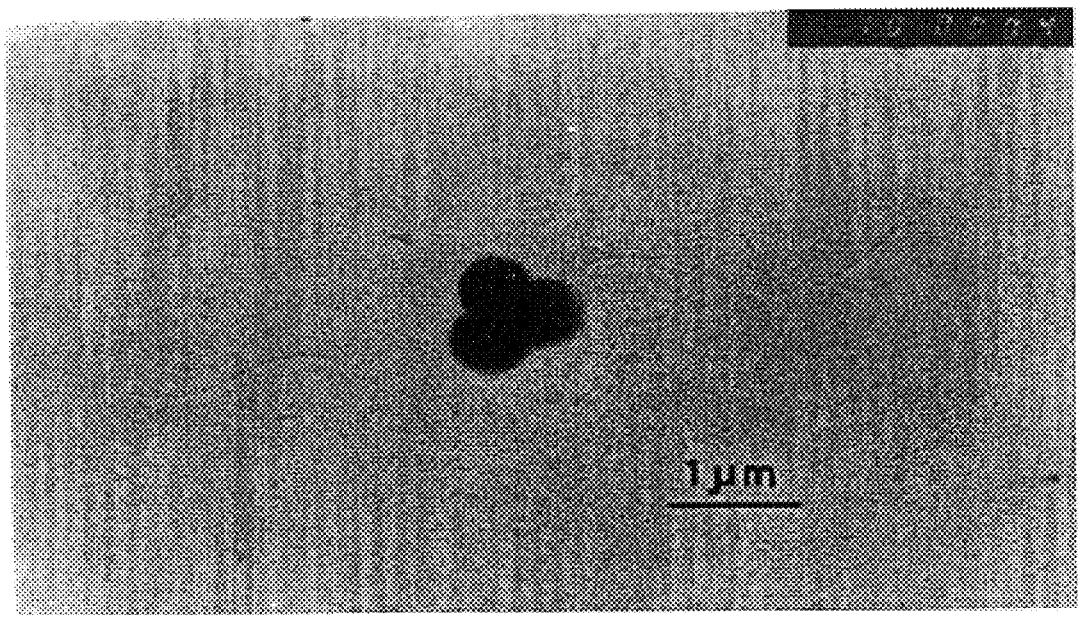

The present invention relates to a process for the microbial production of (4R,6R)-4-hydroxy-2,2,6-trimethylcyclohexanone ("actinol") from (6R)-2,2,6-trimethylcyclohexanedione ("levodione"). Actinol is useful for the synthesis of carotenoids, such as zeaxanthin. More particularly, the present invention relates to a process for the microbial production of actinol utilizing a specific microorganism that is capable of selectively asymmetrically reducing the carbonyl group at the C-4 position of levodione.

BACKGROUND OF THE INVENTION

Actinol has previously been prepared by optical resolution of the diastereomeric mixture of actinol. However, this process requires hydrogenation of levodione by metal catalysts and subsequent optical resolution by chemical means with resolving agents, such as, maleic anhydride (T. Ohashi et al., the proceedings of the symposium "Molecular Chirality 1996" held on May 30 and 31, 1996, in Tokyo, Japan, pages 47 to 50, "Practical Syntheses using Biocatalysts"). Accordingly, this process is not economically feasible for industrial purposes.

Processes of enzymatic preparation of actinol from levodione per se are known. For example, *Bacillus thermophilus* is capable of converting racemic dihydrooxoisophorone to 4 isomers of 4-hydroxy-2,2,6-trimethylcyclohexanone, i.e., to the cis-(4R,6S)-, cis-(4S,6R)-, trans-(4R,6R)- and trans-(4S, 6S)-isomers. The resulting quantitative ratio of these isomers is 68:25:5:2 (J. Biotechnol., 9(2), 117 –128, 1989). Because the content of the (4R,6R)-isomer, actinol, is only 5% of the total isomers, this process is also not economically feasible for industrial purposes.

SUMMARY OF THE INVENTION

As a result of extensive studies on selective asymmetric reduction of levodione, it has surprisingly been found that actinol can be obtained efficiently from levodione by selective asymmetric reduction using certain microorganisms followed by recovery of the actinol from the reaction mixture. The present invention is based upon this finding.

Accordingly, the present invention provides a process for making actinol by contacting levodione with a microorganism, which is selected from the group consisting of microorganisms of the genera Cellulomonas, Corynebacterium, Planococcus and Arthrobacter and which is capable of selective asymmetric reduction of levodione to actinol, and recovering the resulting actinol from the reaction mixture.

DETAILED DESCRIPTION OF THE INVENTION

Screening was effected using a method known per se. For example, a microorganism is cultivated in a nutrient medium containing saccharides, such as, glucose and sucrose, alcohols, such as, ethanol and glycerol, fatty acids, such as, oleic acid and stearic acid or esters thereof, or oils, such as, rapeseed oil and soybean oil as carbon sources; ammonium sulfate, sodium nitrate, peptone, amino acids, corn steep liquor, bran, yeast extract and the like as nitrogen sources; magnesium sulfate, sodium chloride, calcium carbonate, potassium monohydrogen phosphate, potassium dihydrogen phosphate and the like as inorganic salt sources; and malt extract, meat extract and the like as other nutrient sources by a conventional method to provide cells. The cultivation can be carried out aerobically, normally for a cultivation period of 1 to 7 days at a medium pH of 3 to 9 and a cultivation temperature of 10 to 40° C. After the cultivation, the resulting cells are collected by centrifugation or filtration. The cells thus obtained and levodione are brought (contacted) together in a solvent such as water, potassium phosphate buffer, acetonitrile, ethanol and the like, and a reaction is initiated under appropriate reaction conditions (levodion concentration: 400 to 2000 mg/g dry cells/l, pH range: 4 to 9, temperature range: 20 to 50° C., reaction period: 10 minutes to 80 hours). The reaction mixture is extracted with an organic solvent such as ethyl acetate, n-hexane, toluene, n-butyl acetate and the like. The extracted solution is subjected to an appropriate method, such as, chromatography, to measure the productivity of actinol from levodione.

As a result of the screening, it has been found that microorganisms belonging to the genera Cellulomonas, Corynebacterium, Planococcus and Arthrobacter are capable of the selective asymmetric reduction of levodione. Preferred such microorganisms are Cellulomonas sp. AKU672, *Corynebacterium aquaticum* AKU610, *Corynebacterium aquaticum* AKU611, *Planococcus okeanokoites* AKU152 and *Arthrobacter sulfurous* AKU635. Especially preferred are the first three named microorganisms, of which *Corynebacterium aquaticum* AKU611 is most preferred.

The microorganisms Cellulomonas sp. AKU672, *Corynebacterium aquaticum* AKU610 and *Corynebacterium aquaticum* AKU611 were isolated from soil samples collected at Lake Manahime, Fukui Prefecture, Japan. These micoorganisms were deposited with the National Institute of Bioscience and Human-Technology, Agency of Industrial Science and Technology, Japan on Aug. 4, 1998 under the Budapest Treaty and have the following designations: Cellulomonas sp. AKU672 (FERM BP-6449) *Corynebacterium aquaticum* AKU610 (FERM BP-6447) *Corynebacterium aquaticum* AKU611 (FERM BP-6448)

Cellulomonas sp. AKU672, *Corynebacterium aquaticum* AKU610, and *Corynebacterium aquaticum* AKU611 were deposited on Aug. 4, 1998 at the National Institute of Bioscience and Human-Technology, Agency of Industrial Science and Technology (1–3, Higashi 1-Chome, Tsukuba City, Ibaraki Pref., Japan) as FERM BP-6449, FERM BP-6447, FERM BP-6448, respectively under the terms of the Budapest Treaty. All restrictions on public access to these deposits will be irrevocably removed upon the grant of a patent on this application.

These three microorganisms, and also *Planococcus okeanokoites* AKU152 and *Arthrobacter sulfureus* AKU635, are new and represent a further aspect of the present invention.

Figure 2:
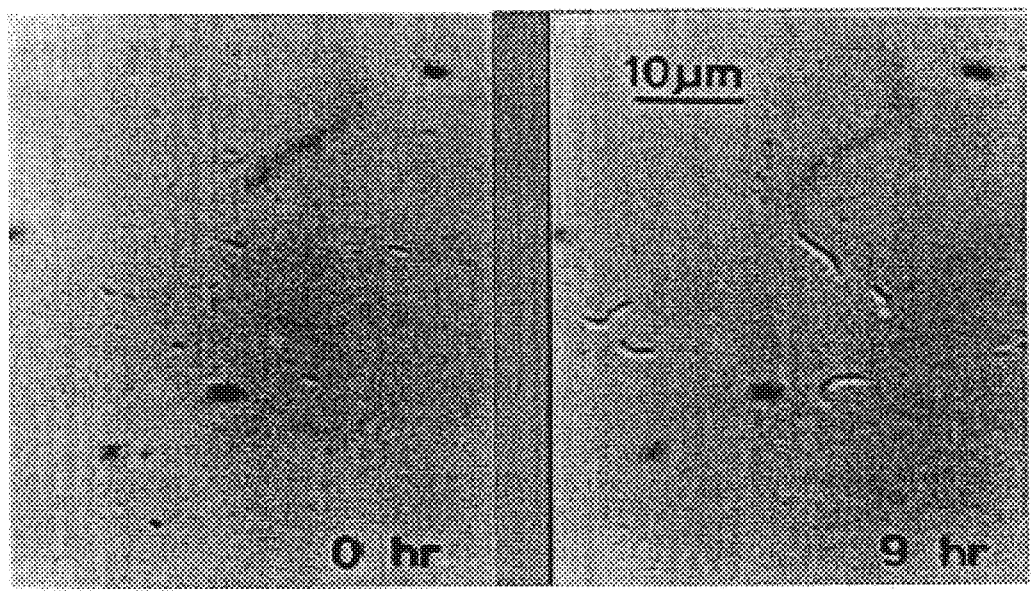

The above-mentioned strain AKU672 (FERM BP-6449) has the following taxonomical properties:

Typical pleomorphism of strain Cellulomonas sp. AKU672 was found on electron microscopic observation. An old culture of the strain was coccoidal as shown in FIG. 1. In young cultures, irregular rods were dominant (FIG. 2). The morphological, physiological and biochemical characteristics of the strain are summarized in Tables I and II.

TABLE I

Morphological and Culture Characteristics of Strain Cellulomonas sp. AKU672

| | |
|---|---|
| Form and size | Coryneform |
| | Old culture; coccoid cells, ca. 0.5–0.6 μm |
| | Fresh culture; irregular rods, 0.5–0.7 μm by 20 or more μm |
| Motility | Motile with one flagellum |
| Gram strain | + |
| Spores | No observation |
| Nutrient agar plate | Circular, convex, smooth, entire, yellow (2 days) |
| Nutrient broth | Ring and slight sediment |
| Gelatin stab | Liquefaction |
| Litmus milk | Acid formation |
| Relation to NaCl | Grow up to 5% NaCl |

TABLE II

Physiological and Biochemical Characteristics of Strain Cellulomonas sp. AKU672

| | |
|---|---|
| Type of cell wall | Ornithine |
| Type of cell division | Bending |
| GC content (%) | 74.7% |
| Hydrolysis of gelatin | + |
| Hydrolysis of starch | + |
| Production of indole | – |
| Production of hydrogen sulfide | – |
| Reduction of nitrate to nitrite | + |
| Utilization of citrate | – |
| Catalase activity | + |
| Oxidase activity | – |
| Urease activity | – |
| DNase activity | + |
| Amino peptidase activity | – |
| Cellulose attack | – |
| Voges-Proskauer test | – |
| Methyl-red test | – |
| Oxidation-Fermentation test* | Fermentation |
| Cleavage of carbohydrates | Acid production but no gas from arabinose, arbutin, cellobiose, dextrin, fructose, galactose, glucose, glycogen, maltose, starch, sucrose, trehalose and xylose; No acid production from glycerol, inulin, lactose, mannitol, mannose, α-methylglucoside, raffinose, rhamnose, sorbitol and sorbose |
| Optimum temperature for growth | 37–42° C. |
| Optimum pH for growth | pH 6.0–7.5 |
| Heating at 63° C. for 30 min. in skimmed milk | Survives |
| Aerobic or anaerobic | Aerobic |

*R. Hugh & E. Leifson, J. Bacteriol. 66, 24(1953)

The strain Cellulomonas sp. AKU672 is gram-positive and aerobic, and can be classified as belonging to the group of "coryneform bacteria". This strain was motile with one flagellum. Ornithine was found in the cell wall as the principal amino acid. Its content according to gas chromatography ("GC") was found to be 74.7%. Bending-like cell division was observed. The strain produced acid from a wide variety of sugars without gas formation for 4 days. This strain did not show cellulolytic activity.

The classification of coryneform bacteria is not well established. Recently, Yamada and Komagata [J. Gen. Appl. Microbiol., 18, 417 (1992)] proposed classifying the coryneform bacteria into seven groups depending on the principal type of cell division, cell wall composition and DNA content according to GC. They differentiated Group 4 from other groups despite the lack of cellulolytic activity. Bacteria of this group exhibit the bending type of cell division, and the principal amino acid in the cell wall is ornithine. Their contents according to GC are distributed in a narrow and high range from 71 to 73%. These bacteria produce acid fermentatively from a wide variety of sugars. According to their proposal, the strain Cellulomonas sp. AKU672, which did not show cellulolytic activity, should belong to Group 4. Other characteristics of the strain on classification coincided well with those of Group 4, and so it has been tentatively named as Cellulomonas sp. AKU672.

The above-mentioned strains AKU610 and AKU611 have the following taxonomical properties:

1) Growable temperature: 15–40° C.
2) Optimum temperature for growth: 30° C.
3) Obligatory aerobic and gram negative microorganism
4) Spore formation: None
5) Polymorphism and traditional rod-cocus cycles can be observed during cultivation.
6) Motility: None Moreover, the strains *Corynebacterium aquaticum* AKU610 and AKU611 were identified as such based on assimilation of various carbon sources by the Biolog System (Biolog Inc., 3447 Investment Blvd., Suite 3, Hayward, Calif. 94545, USA: Nature Vol. 339, 157–158, May 11, 1989) as follows:

Cells of each strain were inoculated with 96-well microtiter-plates and incubated for 24 hours at 28° C. Each well contains one of 96 kinds of carbon sources in BUGM+B medium (Biolog Universal Growth Media+ blood; Biolog Inc.).

After incubation, each strain showed the following assimilation of carbon sources:

| C source | AKU610 | AKU611 | C source | AKU610 | AKU611 |
|---|---|---|---|---|---|
| A1 | – | – | A2 | – | – |
| A3 | – | – | A4 | – | – |
| A5 | – | – | A6 | – | – |
| A7 | – | – | A8 | + | + |
| A9 | + | + | A10 | – | – |
| A11 | – | – | A12 | + | + |
| B1 | – | – | B2 | – | + |
| B3 | – | – | B4 | + | – |
| B5 | + | + | B6 | – | – |
| B7 | + | + | B8 | – | – |
| B9 | + | + | B10 | + | + |
| B11 | + | + | B12 | – | – |
| C1 | – | – | C2 | – | – |
| C3 | – | – | C4 | + | + |
| C5 | + | + | C6 | + | + |
| C7 | + | – | C8 | + | + |
| C9 | – | – | C10 | – | – |
| C11 | – | – | C12 | – | – |
| D1 | – | – | D2 | – | – |
| D3 | + | + | D4 | – | – |
| D5 | + | + | D6 | – | – |
| D7 | – | – | D8 | – | + |
| D9 | – | – | D10 | – | – |
| D11 | + | + | D12 | + | + |
| E1 | – | – | E2 | – | – |
| E3 | + | + | E4 | – | – |
| E5 | – | – | E6 | – | – |
| E7 | – | – | E8 | – | – |
| E9 | – | – | E10 | – | – |
| E11 | – | – | E12 | – | – |
| F1 | – | – | F2 | – | – |

-continued

| C source | AKU610 | AKU611 | C source | AKU610 | AKU611 |
|---|---|---|---|---|---|
| F3 | − | − | F4 | − | − |
| F5 | − | − | F6 | + | + |
| F7 | − | − | F8 | − | − |
| F9 | − | − | F10 | − | − |
| F11 | − | − | F12 | − | − |
| G1 | − | − | G2 | − | − |
| G3 | − | − | G4 | − | − |
| G5 | − | − | G6 | − | − |
| G7 | − | − | G8 | − | − |
| G9 | − | − | G10 | − | − |
| G11 | − | − | G12 | − | − |
| H1 | − | − | H2 | − | − |
| H3 | − | − | H4 | − | − |
| H5 | − | − | H6 | − | − |
| H7 | − | − | H8 | − | − |
| H9 | − | − | H10 | − | − |
| H11 | − | − | H12 | − | − |

A1: water
A2: α-cyclodextrin
A3: β-cyclodextrin
A4: dextrin
A5: glycogen
A6: inulin
A7: mannan
A8: Tween ® 40
A9: Tween ® 80
A10: N-acetyl-D-glucosamine
A11: N-acetyl-D-mannosamine
A12: amygdalin
B1: L-arabinose
B2: D-arabitol
B3: arbutin
B4: cellobiose
B5: D-fructose
B6: L-fucose
B7: D-galactose
B8: D-galacturonic acid
B9: gentiobiose
B10: D-gluconic acid
B11: α-D-glucose
B12: m-inositol
C1: α-D-lactose
C2: lactulose
C3: maltose
C4: maltotriitrose
C5: D-mannitol
C6: D-mannose
C7: D-melezitose
C8: D-melibiose
C9: α-methyl-D-galactoside
C10: α-methyl-D-galactoside
C11: 3-methyl-glucose
C12: α-methyl-D-glucoside
D1: β-methyl D-glucoside
D2: α-methyl D-mannoside
D3: palatinose
D4: D-psicose
D5 D-raffinose
D6: L-rhamnose
D7: D-ribose
D8: salicin
D9: sedoheputulosan
D10: D-sorbit
D11: stachyose
D12: sucrose
E1: D-tagatose
E2: D-trehalose
E3: turanose
E4: xylitol
E5: D-xylose
E6: acetic acid
E7: α-hydroxybutyric acid
E8: β-hydroxybutyric acid
E9: γ-hydroxybutyric acid
E10: p-hydroxyphenylacetic acid
E11: α-keto-glutaric acid
E12: α-keto-valeric acid
F1: lactamide
F2: D-lactic acid methyl ester
F3: L-lactic acid
F4: D-malic acid
F5: L-malic acid
F6: methyl pyruvate
F7: monomethyl succinate
F8: propionic acid
F9: pyruvic acid
F10: succinamic acid
F11: succinic acid
F12: N-acetyl-L-glutamic acid
G1: alaninamide
G2: D-alanine
G3: L-alanine
G4: L-alanyl-glycine
G5: L-asparagine
G6: L-glutamic acid
G7: glycyl-L-glutamic acid
G8: L-pyloglutamic acid
G9: L-serine
G10: putrscine
G11: 2,3-butanediol
G12: glycerol
H1: adenosine
H2: 2'-deoxy adenosine
H3: inosine
H4: thymidine
H5: uridine
H6: adenosine-5'-monophosphate
H7: thymidine-5'-monophosphate
H8: uridine-5'-monophosphate
H9: fructose-6-phosphate
H10: glucose-1-phosphate
H11: glucose-6-phosphate
H12: DL-α-glycerol phosphate From the above results, both strains are identified as *Corynebacterium aquaticum* and named *Corynebacterium aquaticum* AKU610 and AKU611, respectively.

Other microorganisms mentioned above are available from a public depositary (culture collection) to anyone upon request, such as the Institute of Fermentation Osaka, Japan (IFO). Examples of such deposited strains are *Planococcus okeanokoites* AKU152 (IFO 15880) and *Arthrobacter sulfureus* AKU635 (IFO 12678).

The selective asymmetric reduction process of the present invention can be carried out batchwise, semibatchwise or continuously in water or in a solvent medium that is miscible with water, enhances levodione solubility and is inert to the enzyme reaction, such as, 0.01 to 0.5M potassium phosphate buffer, another buffer with the pH range 4 to 10, acetonitrile, ethanol or N,N-dimethylformamide. The concentration of levodione is conveniently 400 to 2000 mg/1 g dry cells/l, preferably 400 to 800 mg/1 g dry cells/l. The selective asymmetric reduction process may be carried out in a pH range from 4 to 9, preferably from 6 to 7, in a temperature range from 20 to 50° C., preferably 30 to 40° C., and for 10 minutes to 80 hours, preferably for 8 hours to 24 hours.

The selective asymmetric reduction process of the present invention is conveniently carried out in the presence of a co-factor such as nicotinamide adenine dinucleotide (NAD), nicotinamide adenine dinucleotide phosphate (NADP), or said co-factor with glucose and glucose dehydrogenase (GDH). The concentration of such co-factor in the reaction medium is preferably 300 mM/l or more, more preferably from 700 mM/l to 900 mM/l. Moreover, the yield of actinol can be increased by addition of a surfactant to the reaction mixture. Span® 20, Span® 80, Tween® 20, Tween® 40 (all available from Wako Pure Chemical Ind., 3-1-2 Doshomachi, Osaka, Japan) and the like are examples of surfactants that can be used. The amount of surfactant in the reaction medium is conveniently 2 to 20 mM/l, preferably about 8 mM/l.

After selective asymmetric reduction has been completed, the actinol thus obtained can be recovered by extraction with a water-insoluble (water- immiscible) organic solvent that readily solubilizes actinol, such as, ethyl acetate, n-hexane, toluene or n-butyl acetate. Further purification of actinol can be effected by concentrating the extract to directly crystallize the actinol or by the combination of various kinds of chromatography, such as, thin layer chromatography, adsorption chromatography, ion-exchange chromatography and/or gel filtration chromatography. If necessary, high performance liquid chromatography can also be applied. A preferred recovery leading to crystals of actinol involves extracting the actinol with ethyl acetate and concentrating the extract to obtain actinol crystals.

As an alternative to the above described "resting cell reaction" technique, actinol can be produced by fermentation of the above microorganisms in a nutrient medium in the presence of levodione, i.e., in a "growing cell reaction". Both alternatives are embraced by the process of the present invention.

As nutrient media in the "growing cell reaction" technique there may be used those which contain saccharides, such as, glucose and sucrose, alcohols, such as, ethanol and glycerol, fatty acids, such as, oleic acid and stearic acid or esters thereof, or oils, such as, rapeseed oil and soybean oil as carbon sources; ammonium sulfate, sodium nitrate, peptone, amino acids, corn steep liquor, bran, yeast extract and the like as nitrogen sources; magnesium sulfate, sodium chloride, calcium carbonate, potassium monohydrogen phosphate, potassium dihydrogen phosphate and the like as inorganic salts; and malt extract, meat extract and the like as other nutrient sources. As a further aspect of the present invention, actinol can be produced by fermentation of the above microorganisms in a nutrient medium in the presence of levodione.

The fermentation can be carried out aerobically, normally for an incubation period of 1 to 7 days at a medium pH of 3 to 9 and a fermentation temperature of 10 to 40° C.

The microorganisms to be used in the fermentation may be in any form, for example, cultures obtained by fermentation of strains in liquid media, cells separated from liquid cultures, dried cells obtained by processing cells or cultures, or immobilized cells.

The following Examples illustrate the present invention.

EXAMPLE 1

A liquid medium (pH 7.0) having 0.5% 1,4-cyclohexanedione (structurally analogous to (6R)-2,2,6-trimethylcyclohexanedione; used for the screening), 0.5% Tween® 20, 0.1% $(NH_4)_2SO_4$, 0.1% $K_2HPO_4$, 0.02% $MgSO_4.7H_2O$ and 0.02% yeast extract was dispersed in 5 ml portions into test tubes, and then sterilized at 121° C. for 20 minutes. About 0.3 g of soil sample was introduced into each of these tubes and cultivated for 24 hours at 30° C. A 0.1 ml portion of the culture thus obtained was used to inoculate fresh test tube medium as above, and this operation was repeated twice. The enriched culture thus obtained was diluted with saline and spread on an agar medium having the same ingredients as above. Simultaneously, supernatant of the soil suspension in saline was appropriately diluted and spread on the agar medium as well. The plates were incubated for 48 hours at 30° C. Grown colonies on the plates were used to inoculate 5 ml liquid medium (pH 7.0) having 1.0% glucose, 0.3% $K_2HPO_4$, 0.02% $MgSO_4.7H_2O$, 1.5% peptone (Mikuni Kagaku Sangyo K. K., 4-1-6 Muro-machi, Nihonbashi, Chuo-ku,Tokyo, Japan), 0.2% NaCl and 0.1% yeast extract (Nacalai Tesuque Inc., Karasumaru Nishihairu, Nijohtouri, Nakakyo-ku, Kyoto, Japan) in a tube. After the tubes had been incubated at 30° C. for 24 hours, cells were collected by centrifugation and washed with saline. The cells thus obtained were subjected for the subsequent screening. In addition to the above microorganisms, air-dried cells of the microorganisms that had been cultivated in a nutrient medium were also used for the screening.

EXAMPLE 2

A reaction mixture (pH 7.0 in 0.1 M potassium phosphate buffer) containing 0.6 mg of NAD (Oriental Yeast Co., 3-6-10 Azusawa, Itabashi-ku, Tokyo, Japan), 0.6 mg of NADP (Oriental Yeast Co.), 50 mg of D-glucose and 0.2 mg of D-glucose dehydrogenase (Amano Pharmaceutical Co., 1-2-7 Nishiki, Naka-ku, Nagoya, Japan) was prepared. About 0.3 g of the cells prepared in Example 1 was added to 1 ml of the reaction mixture, followed by a sufficient amount of (6R)-2,2,6-trimethylcyclohexanedione to give a final concentration of 0.5%. The reaction mixture was then incubated with shaking for 24 hours at 30° C. After incubation, the reaction mixture was extracted with 1 ml of ethyl acetate and concentrated. The yield and the optical purity of the (4R, 6R)-4-hydroxy-2,2,6-trimethylcyclohexanone were analyzed by gas chromatography [column: HR-20M (Shinwa Chemical Ind., Keishyo-cho 50, Fushimi-ku, Kyoto, Japan) 0.25 mmϕ×30 m, column temperature: 160° C. (constant), injector temperature: 250° C., carrier gas: He (approx. 1 ml/min)]. The results are presented in Table III.

TABLE III

| Strain Name | Rate of reduction (%) | Optical purity of (4R, 6R)-4-hydroxy-2,2,6-trimethyl-cyclohexanone (% e.e.) |
|---|---|---|
| *Planococcus okeanokoites* AKU152 (IFO 15880) | 42.3 | 56.7 |
| *Arthrobacter sulfureus* AKU635 (IFO 12678) | 64 | 44 |
| *Cellulomonas sp.* AKU672 (FERM BP-6449) | 73 | 78.3 |
| *Corynebacterium aquaticum* AKU610 (FERM BP-6447) | 93.7 | 85.9 |
| *Corynebacterium aquaticum* AKU611 (FERM BP-6448) | 97.4 | 87.7 |

EXAMPLE 3

The effect of the addition of NAD or NADP to the reaction mixture was elucidated by using the microorganisms given in Table III. The basic reaction mixture contained all the components described in Example 2 except NAD and NADP. The cells of the microorganisms used in the present Example were air-dried, and 10 mg of the cell mass were incorporated into the reaction mixture. The reaction was carried out at 30° C. for 24 hours. The results are presented in Table IV, in which the optical purity (% e.e.) values apply to the (4R,6R)-isomer, as is also the case in Tables V (Example 4) and VI (Example 5).

TABLE IV

| | Co-factor Addition | | | | | |
|---|---|---|---|---|---|---|
| | NAD | | NADP | | None | |
| Strain Name | Rate of reduction (%) | Optical purity (% e.e.) | Rate of reduction (%) | Optical purity (% e.e.) | Rate of reduction (%) | Optical purity (% e.e.) |
| Planococcus okeanokoites AKU152 (IFO 15880) | 89.3 | 60.4 | 65.4 | 54.7 | 63.4 | 58.2 |
| Arthrobacter sulfureus AKU635 (IFO 12678) | 82.7 | 24 | 66.5 | −7.3 | 56.5 | −9.5 |
| Cellulomonas sp. AKU672 (FERM BP-6449) | 59.2 | 67.1 | 30.1 | 21.6 | 24.8 | 25.7 |
| Corynebacterium aquaticum AKU610 (FERM BP-6447) | 62.5 | 87.4 | 60 | 85.3 | 17 | 52.1 |
| Corynebacterium aquaticum AKU611 (FERM BP-6448) | 96.8 | 93.9 | 85.3 | 88.5 | 92.5 | 89.1 |

EXAMPLE 4

The effect of the addition of various surfactants (final concentration: 0.1 w/v %) in the reaction mixture was elucidated by using the microorganisms given in Table III. The basic reaction mixture contained all the components described in Example 2. The cells of the microorganisms used in the present Example were air-dried, and 10 mg of the cell mass were incorporated into the reaction mixture. The reaction was carried out at 30° C. for 24 hours. The results are presented in Table V.

EXAMPLE 5

The influence of the substrate concentration on the reaction was elucidated at concentrations of 0.5, 1.0 and 1.5%. The basic reaction mixture contained all the components described in Example 2. In the present Example, the cells of Corynebacterium aquaticum AKU611 (FERM BP-6448) were air-dried, and 10 mg of the cell mass were incorporated into the reaction mixture. The reaction was carried out at 30° C. for 24 hours. The results are represented in Table VI.

TABLE V

| | Surfactant | | | | | | | | | |
|---|---|---|---|---|---|---|---|---|---|---|
| | None | | Tween ® 20 | | Tween ® 40 | | Span ® 20 | | Span ® 80 | |
| Strain Name | Rate of reduction (%) | Optical purity (% e.e.) | Rate of reduction (%) | Optical purity (% e.e.) | Rate of reduction (%) | Optical purity (% e.e.) | Rate of reduction (%) | Optical purity (% e.e.) | Rate of reduction (%) | Optical purity (% e.e.) |
| Planococcus okeanokoites AKU152 (IFO 15880) | 53.9 | 51.6 | 78.1 | 63.4 | 63.9 | 57.7 | 71.4 | 65.7 | 57.3 | 57.3 |
| Arthrobacter sulfureus AKU635 (IFO 12678) | 73.4 | 25.1 | 86.8 | 38.6 | 82.4 | 33.8 | 78.5 | 49.9 | 65.2 | 32 |
| Cellulomonas sp. AKU672 (FERM BP-6449) | 32.3 | 80 | 32.1 | 86.2 | not measured (n.m.) | n.m. | 22.2 | 66.2 | 38 | 78.1 |
| Corynebacterium aquaticum AKU610 (FERM BP-6447) | 58.9 | 87.6 | 71.7 | 89.3 | n.m. | n.m. | 64.6 | 89.9 | 83 | 87.3 |
| Corynebacterium aquaticum AKU611 (FERM BP-6448) | 85.7 | 92.6 | 97.5 | 93.7 | n.m. | n.m. | 96.7 | 94 | 88.8 | 93.2 |

TABLE VI

| Substrate Concentration (%) | Rate of reduction (%) | Optical purity (% e.e.) | Product concentration (%) |
|---|---|---|---|
| 0.5 | 92.2 | 93.0 | 0.46 |
| 1.0 | 73.1 | 92.9 | 0.73 |
| 1.5 | 66.3 | 92.8 | 0.99 |

EXAMPLE 6

*Corynebacterium aquaticum* AKU611 (FERM BP-6448) was cultivated for 24 hours at 30° C. in 20 l of the culture medium containing 0.1% yeast extract, 1.5% peptone, 2.0% D-glucose, 0.02% $MgSO_4.7H_2O$, 0.3% $K_2HPO_4$ and 0.2% NaCl using a 30 l jar fermentor with agitation at 400 rpm and aeration of 0.5 l per minute. Cells were collected from the culture by centrifugation at 5,000 g for 5 minutes thereafter. The weight of the paste of cells thus obtained was 400 g.

Then, 12 g of levodione and 120 g of D-glucose were added to the cell paste and the volume was brought to 2.4 l with ion exchanged water. The pH was adjusted to 7.0 with 2.0% NaOH solution. The reaction mixture was transferred into a 2 l flask and incubated at 30° C. for 15 hours with shaking at 220 rpm. After the incubation, the reaction mixture was separated by centrifugation at 12,000 g for 5 minutes. The volume of the reaction mixture thus obtained was 2.2 l, and the optical purity, the yield and the concentration of actinol were 96% e.e., 93% and 4.6 g/l, respectively.

EXAMPLE 7

The reaction mixture (10 l), prepared as described in Example 6, was mixed with ethyl acetate (10 l) to extract actinol. The ethyl acetate phase (7.5 l) was separated and 350 g of active carbon powder were added thereto for decolorizing it. After stirring for 10 minutes, the carbon powder was removed by filtration. 600 g of anhydrous $Na_2SO_4$ were added to the 6.5 l of ethyl acetate solution for dehydration. After a few minutes of stirring, $Na_2SO_4$ was removed by filtration. The ethyl acetate solution (6.0 l) was concentrated to 50 ml under reduced pressure at 30° C. 5 l of n-hexane were added to the concentrate thus obtained and the mixture was stirred for five minutes, then cooled to 5° C. and maintained at this temperature for 12 hours to crystallize actinol. The crystallized actinol was collected by filtration and then dried. The weight of actinol crystals thus obtained was 32 g, and the purity, the optical purity and the yield of actinol were 96%, 96% e.e and 70%, respectively.

EXAMPLE 8

Seed culture broth (150 ml) of *Corynebacterium aquaticum* AKU611 (FERM BP-6448) was inoculated into 3 l of the fermentation medium containing 0.1% yeast extract, 1.5% peptone, 2.0% glucose, 0.02% $MgSO_4.7H_2O$, 0.3% $K_2HPO_4$, 0.2% NaCl and 0.3% levodione. The fermentation was carried out for 48 hours at 30°C. using a 5 l jar fermentor with agitation at 250 rpm and aeration of 1.5 l per minute. The pH of the fermentation broth was controlled at 7.0 by $NH_3$ gas. After fermentation, the broth was removed and the cells were collected by centrifugation at 12,000 g for 5 minutes. The optical purity, the yield and the concentration of actinol in the broth were 96% e.e., 71% and 2.1 g/l respectively.

What is claimed is:

1. A process for making (4R, 6R)-4-hydroxy-2,2,6-trimethylcyclohexanone, which comprises contacting (6R)-2,2,6-trimethylcyclohexanedione with a microorganism, which is selected from the group consisting of Cellulomonas sp. AKU672 (FERM BP-6449), *Corynebacterium aquaticum* AKU610 (FERM BP-6447), and *Corynebacterium aquaticum* AKU611 (FERM BP-6448), and which is capable of the selective asymmetric reduction of (6R)-2,2,6-trimethylcyclohexanedione to (4R, 6R)-4-hydroxy-2,2,6-trimethylcyclohexanone, and recovering the resulting (4R, 6R)-4-hydroxy-2,2,6-trimethylcyclohexanone from the reaction mixture.

2. A process for making (4R, 6R)-4-hydroxy-2,2,6-trimethylcyclohexanone, which comprises contacting (6R)-2,2,6-trimethylcyclohexanedione with a microorganism, which is *Corynebacterium aquaticum* AKU611 (FERM BP-6448), and which is capable of the selective asymmetric reduction of (6R)-2,2,6-trimethylcyclohexanedione to (4R, 6R)-4-hydroxy-2,2,6-trimethylcyclohexanone, and recovering the resulting (4R, 6R)-4-hydroxy-2,2,6-trimethylcyclohexanone from the reaction mixture.

* * * * *